United States Patent
Cawthra, Jr.

(10) Patent No.: US 7,463,932 B2
(45) Date of Patent: Dec. 9, 2008

(54) FASTENING DEVICE FOR AN EPICARDIAL LEAD

(75) Inventor: James K. Cawthra, Jr., Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 318 days.

(21) Appl. No.: 11/035,775

(22) Filed: Jan. 14, 2005

(65) Prior Publication Data
US 2006/0161237 A1    Jul. 20, 2006

(51) Int. Cl.
*A61N 1/05* (2006.01)

(52) U.S. Cl. .................. 607/115; 607/122; 607/126; 607/128; 607/129; 607/130; 607/149

(58) Field of Classification Search .............. 607/115, 607/122, 126, 128, 129, 130, 149, 123, 119, 607/127; 600/374
See application file for complete search history.

(56) References Cited

U.S. PATENT DOCUMENTS

| | | | |
|---|---|---|---|
| 3,993,049 A * | 11/1976 | Kater | 600/391 |
| 4,177,818 A * | 12/1979 | De Pedro | 607/130 |
| 4,610,251 A | 9/1986 | Kumar | |
| 4,913,164 A * | 4/1990 | Greene et al. | 607/126 |
| 4,955,898 A | 9/1990 | Matsutani et al. | |
| 5,300,107 A * | 4/1994 | Stokes et al. | 607/126 |
| 5,300,110 A * | 4/1994 | Latterell et al. | 607/130 |
| 5,514,174 A | 5/1996 | Heil, Jr. et al. | |
| 5,690,648 A * | 11/1997 | Fogarty et al. | 606/129 |
| 5,725,554 A | 3/1998 | Simon et al. | |
| 5,829,662 A | 11/1998 | Allen et al. | |
| 6,726,695 B2 | 4/2004 | Tong | |
| 6,790,229 B1 | 9/2004 | Berreklouw | |
| 7,128,747 B2 * | 10/2006 | Ginn | 606/108 |
| 2004/0111101 A1 | 6/2004 | Chin | |
| 2004/0176830 A1 * | 9/2004 | Fang | 607/129 |

* cited by examiner

*Primary Examiner*—Carl H Layno
*Assistant Examiner*—Natasha N Patel
(74) *Attorney, Agent, or Firm*—Faegre & Benson LLP

(57) ABSTRACT

An epicardial pacing lead including a flexible, elongated lead body. The epicardial pacing lead has a proximal end and a distal end. An electrode is coupled to the lead body near the distal end. A housing is coupled to the lead body proximal to the electrode. A platform is at least partially encompassed by the housing. The platform includes at least four tines. Each tine is adapted for engagement with the epicardium and includes an upper section extending outwardly from the platform and a lower section extending distally at an angle to the upper section.

19 Claims, 9 Drawing Sheets

FASTENING DEVICE FOR AN EPICARDIAL LEAD

TECHNICAL FIELD

The present invention relates to cardiac leads used in combination with a cardiac function management device such as a heart pacemaker or defibrillator to monitor and control the rhythm of the heart. The present invention more particularly relates to fasteners used to attach the cardiac lead to the epicardial heart surface.

BACKGROUND

Cardiac function management systems are used to treat heart arrhythmias. Pacemaker systems are commonly implanted in patients to treat bradycardia (i.e., abnormally slow heart rate). A pacemaker system includes an implantable pulse generator and leads, which form the electrical connection between the implantable pulse generator and the heart. An implantable cardioverter defibrillator ("ICD") is used to treat tachycardia (i.e., abnormally rapid heart rate). An ICD also includes a pulse generator and leads that deliver electrical energy to the heart.

The leads coupling the pulse generators to the cardiac muscle are commonly used for delivering an electrical pulse to the cardiac muscle, for sensing electrical signals produced in the cardiac muscle, or for both delivering and sensing. The leads are susceptible to categorization according to the type of connection they form with the heart. An endocardial lead includes at least one electrode at or near its distal tip adapted to contact the endocardium (i.e., the tissue lining the inside of the heart). An epicardial lead includes at least one electrode at or near its distal tip adapted to contact the epicardium (i.e., the tissue lining the outside of the heart). Finally, a myocardial lead includes at least one electrode at or near its distal tip inserted into the heart muscle or myocardium (i.e., the muscle sandwiched between the endocardium and epicardium).

The lead typically consists of a flexible conductor surrounded by an insulating tube or sheath that extends from the electrode at the distal end to a connector pin at the proximal end. The lead electrode at the distal end is attached to the heart tissue using a fastening device. Fastening devices currently known in the art include a helix, which is screwed into the epicardial tissue. There is a need for an electrode fastening device that provides for quick and secure placement and enhances attachment success.

SUMMARY

An epicardial pacing lead comprising a flexible, elongated lead body having a proximal end and a distal end; an electrode coupled to the lead body near the distal end; a housing coupled to the lead body proximal to the electrode; and a platform at least partially encompassed by the housing, the platform including at least four tines, each tine adapted for engagement with the epicardium and including an upper section extending outwardly from the platform and a lower section extending distally at an angle to the upper section.

A method of using an epicardial pacing lead comprising providing an epicardial pacing lead comprising a flexible, elongated lead body having a proximal end and a distal end, an electrode coupled to the lead body near the distal end, a housing coupled to the lead body proximal to the electrode, and a platform at least partially encompassed by the housing, the platform including at least four tines, each tine including an upper section extending outwardly from the platform and a lower section extending distally at an angle to the upper section; inserting the platform into an attachment device having a support section and a bending section slideably engaged with the support section so that the support section holds the platform; positioning the platform adjacent to the epicardium so that the tines are positioned to pierce the epicardium; and actuating the bending section so that the bending section slides past the support section and forces the lower section of the tines into the epicardium, thereby attaching the platform to the epicardium.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
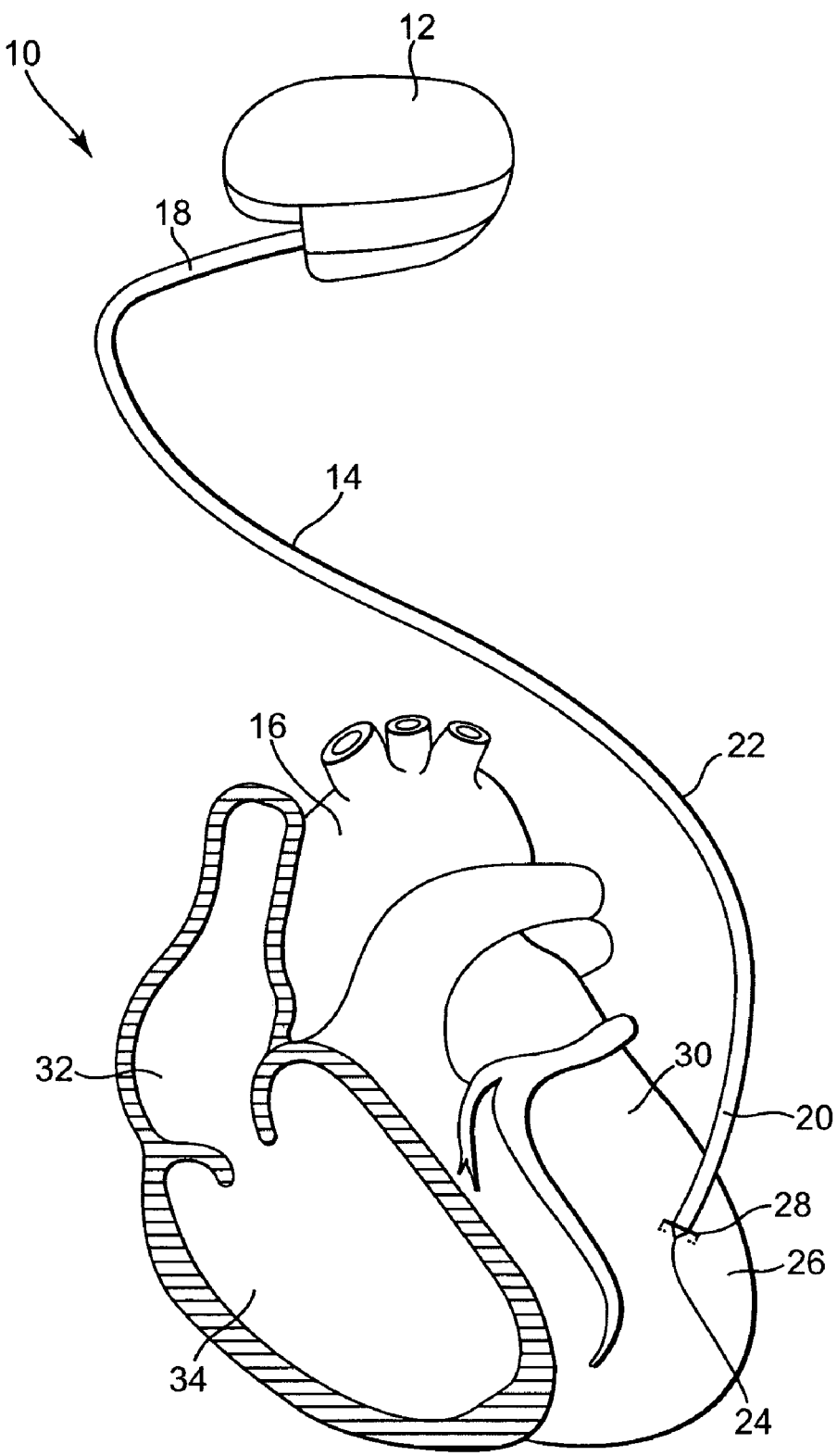
FIG. 1 shows a perspective view of an implantable cardiac function management system according to the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of a cardiac function management system 10. The system 10 includes a pulse generator 12 and a cardiac lead 14. The lead 14 operates to convey electrical signals between the heart 16 and the pulse generator 12. A proximal end 18 of the lead 14 is coupled to the pulse generator 12 and a distal end 20 is coupled to the heart 16. The lead 14 includes a lead body 22 extending from the lead proximal end 18 to the lead distal end 20.

As shown in FIG. 1, an electrode 24 is attached to the epicardium 26 of heart 16 by the fastening device 28. When positioned as above, the electrode 24 can be used to sense the electrical activity of the heart 16 or to apply a stimulating pulse to the left ventricle 30. In other embodiments, the cardiac lead 14 of the present invention can also be implanted in any other portion of the heart as known in the art of cardiac function management. For example, it may be implanted in the right atrium 32 or the right ventricle 34.

Figure 2A:
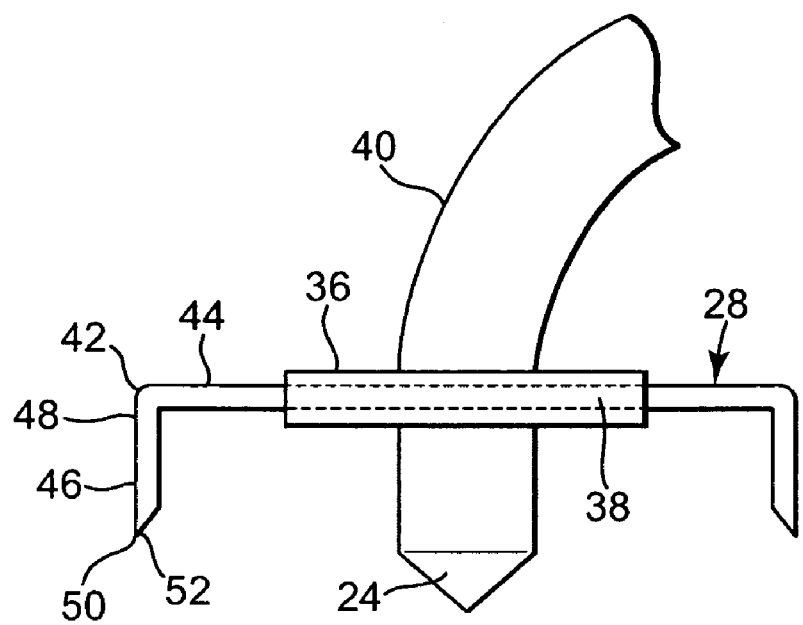
FIG. 2A shows a side plan view of a fastening device according to one embodiment of the present invention.

FIG. 2A is a side plan view of one embodiment of the fastening device 28. In this embodiment, the fastening device 28 includes a housing 36 and a platform 38 which is partially encompassed by the housing 36. The housing 36 can be integral with the lead insulation 40. The platform 38 includes tines 42. The tines 42 include upper sections 44 and lower sections 46. The upper sections 44 extend outwardly from the platform 38. As shown in FIG. 2A, the upper sections 44 are substantially parallel with the platform 38 and the lower sections 46 are bent at an angle of approximately 90 degrees to the upper sections 44. The lower sections 46 include proximal ends 48 and distal ends 50. Points 52 for piercing the epicardium can be located at the distal ends 50.

Alternatively, the upper sections 44 need not be substantially parallel to the platform 38, but instead may be bent at some other angle to the platform 38. The lower sections 46 may also be bent at some angle other than 90 degrees to the upper sections 44. In one embodiment, the angle between the upper sections 44 and the lower sections 46 can range from approximately 70 to approximately 120 degrees. The platform 38 and tines 42 can be made out of any malleable metal, such as stainless steel. The tines may be straight, as is shown in FIG. 2A, or may be curved.

Figure 2B:
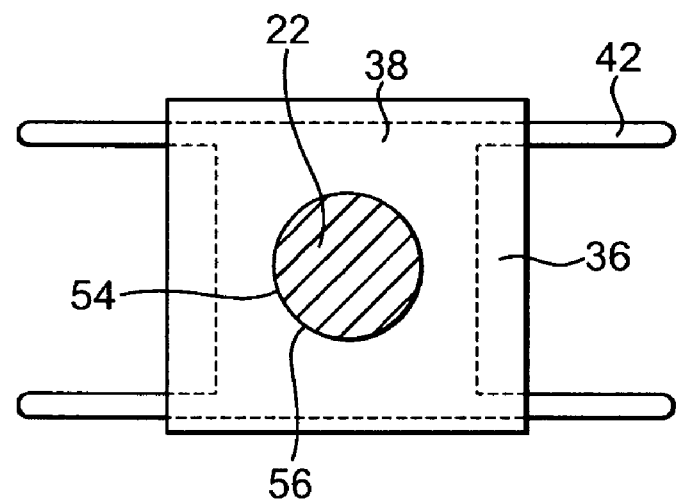
FIG. 2B shows a top plan view of the fastening device of FIG. 2A.

FIG. 2B is a top plan view of the fastening device 28 of FIG. 2A. The housing 36 includes an aperture 54 through which the lead body 22 passes. There is a corresponding aperture 56 in the platform 38. As shown in FIG. 2A, the platform 38 has a substantially rectangular shape and also the housing 36 has a substantially rectangular shape. Alternatively, the housing 36 could have any other shape suitable for partially encompassing the platform 38. The housing 36 can be made out of silicone or polyurethane. The housing 36 can be made out of any other material suitable for retaining the lead body 22. Four tines 42 are shown in FIGS. 2A and 2B, but the number of tines 42 may vary as needed. In one embodiment, the penetration of the electrode 24 into the epicardium 26 can range from approximately 0 to 10 millimeters. In one embodiment, the ratio of the length of the platform 38 to the diameter of the lead body 22 can vary between about 2:1 and about 4:1.

Figure 3A:
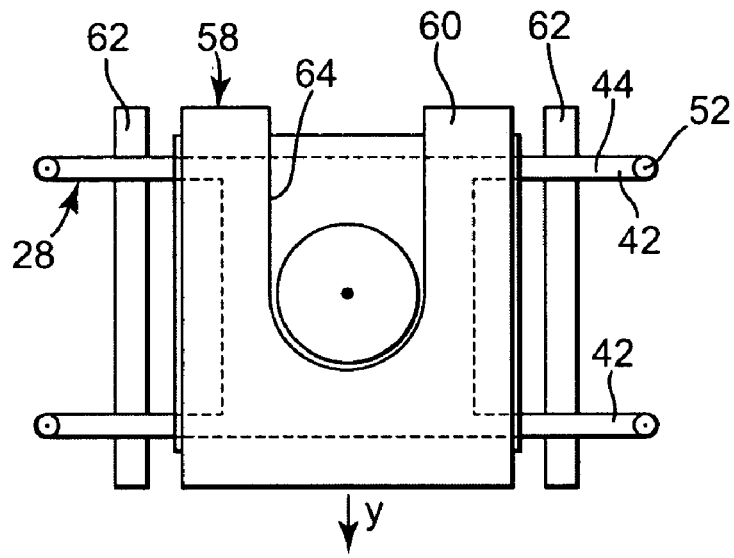
FIG. 3A shows a bottom plan view of the fastening device of FIG. 2A positioned in an attachment device prior to attachment.

FIG. 3A is a bottom plan view of the fastening device 28 of FIG. 2A after the fastening device 28 has been slideably inserted in an attachment device 58. One such attachment device is disclosed in U.S. Pat. No. 5,829,662 to Allen, et al., which is hereby incorporated by reference. As shown, the attachment device 58 includes a support section 60 and bending sections 62. The fastening device 28 is interposed between the support section 60 and the bending sections 62. The bending sections 62 overlay the tines 42. During deployment, the platform 38 of the fastening device 28 is positioned so tines 42 can pierce the epicardium 26. The support section 60 includes an opening 64 adapted to fit around the lead body 22.

Figure 3B:
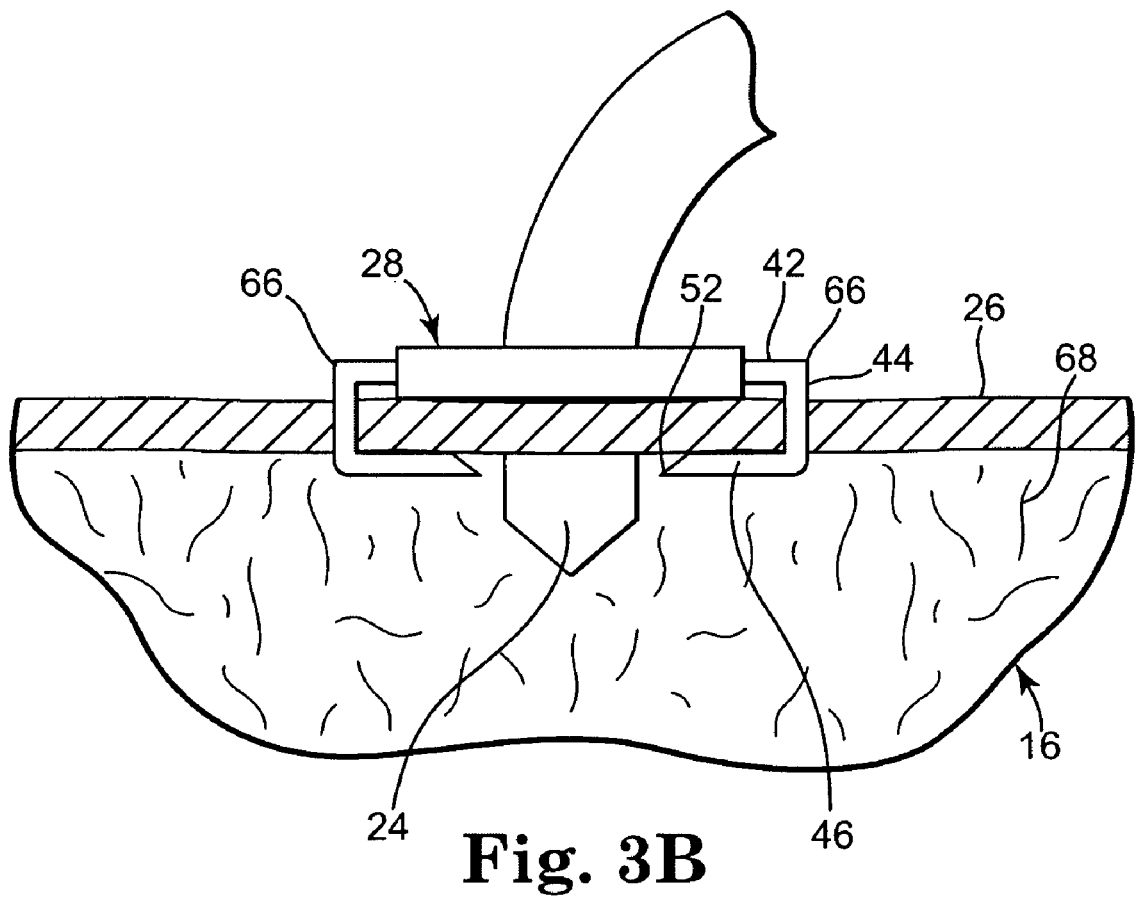
FIG. 3B shows a side plan view of the fastening device of FIG. 2A after the fastening device has been attached to the epicardial tissue.

FIG. 3B shows a side plan view of the fastening device of FIG. 2A in a deformed or deployed configuration. When a force is applied to the attachment device 58 so that the bending sections 62 slide past the support section 60 toward the epicardium 26, the upper sections 44 of tines 42 are bent, creating a bend 66. As shown in FIG. 3B, this bending forces the points 52 of lower sections 46 through the epicardium 26 and into the myocardium 68, thereby attaching the fastening device 28 and the electrode 24 to the heart 16. After attachment, the support section 60 of the attachment device 58 can then be slid in direction y (as shown in FIG. 3A) and the fastening device 28 is thereby released from the attachment device 58.

Figure 4A:
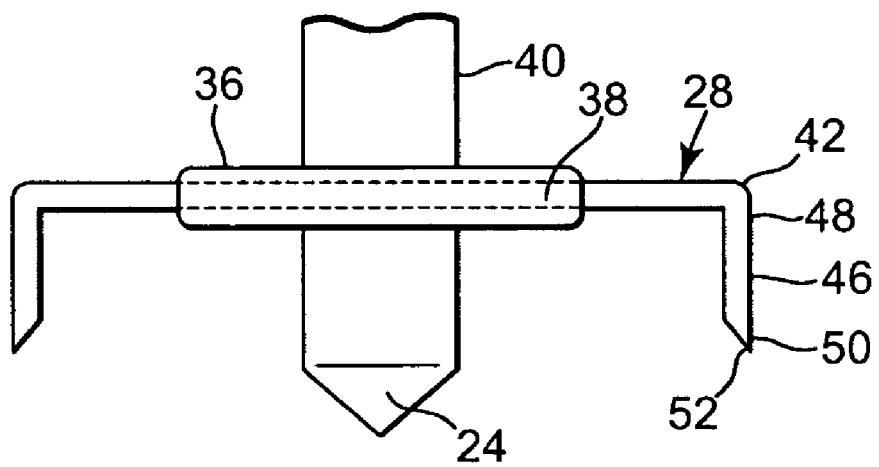
FIG. 4A shows a side plan view of another embodiment of the present invention.
Figure 4B:
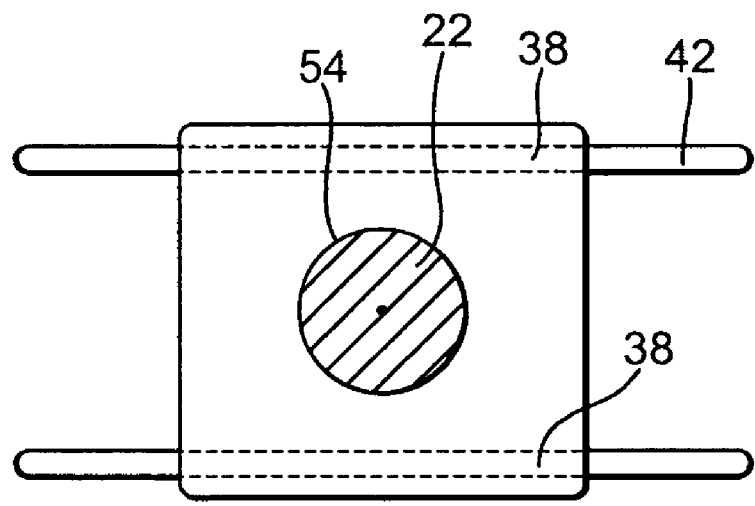
FIG. 4B shows a top plan view of the fastening device of FIG. 4A.

FIG. 4A shows an alternative embodiment of the present invention. In this embodiment, the housing 36 partially encompasses two platforms 38. Each platform 38 includes tines 42. The tines 42 include upper sections 44 and lower sections 46. The upper sections 44 extend outwardly from the platforms 38. The lower sections 46 include proximal ends 48 and distal ends 50. The distal ends 50 can include points 52 for piercing the epicardium. As shown in FIG. 4B, the housing 36 includes an aperture 54 through which the lead body 22 passes. Although four tines 42 are shown in FIGS. 4A and 4B, the number of tines 42 may vary. The angle between the upper sections 44 and the lower sections 46, as well as the angle between the upper sections 44 and the platforms 38 may also vary. In one embodiment, the angle between the upper sections 44 and the lower sections 46 can range from approximately 70 to approximately 120 degrees. In one embodiment, the penetration of the electrode 24 into the epicardium 26 can range from approximately 0 to 10 millimeters. In one embodiment, the ratio of the length of the platforms 38 to the diameter of the lead body 22 can vary between about 2:1 and about 4:1.

Figure 5A:
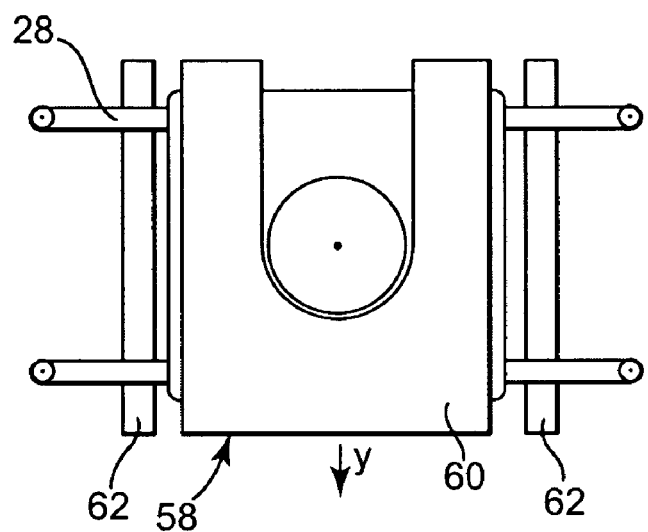
FIG. 5A shows a bottom plan view of the fastening device of FIG. 4A positioned for attachment in the attachment device prior to attachment.

FIG. 5A is a bottom plan view of the fastening device 28 of FIG. 4A after the fastening device 28 has been slideably inserted in the attachment device 58. The attachment device 58 includes a support section 60 and a bending sections 62. The fastening device 28 is interposed between the support section 60 and the bending sections 62. During deployment, the support section 60 is located adjacent to the epicardium 26. The support section 60 includes an opening 64 adapted to fit around the lead body 22.

Figure 5B:
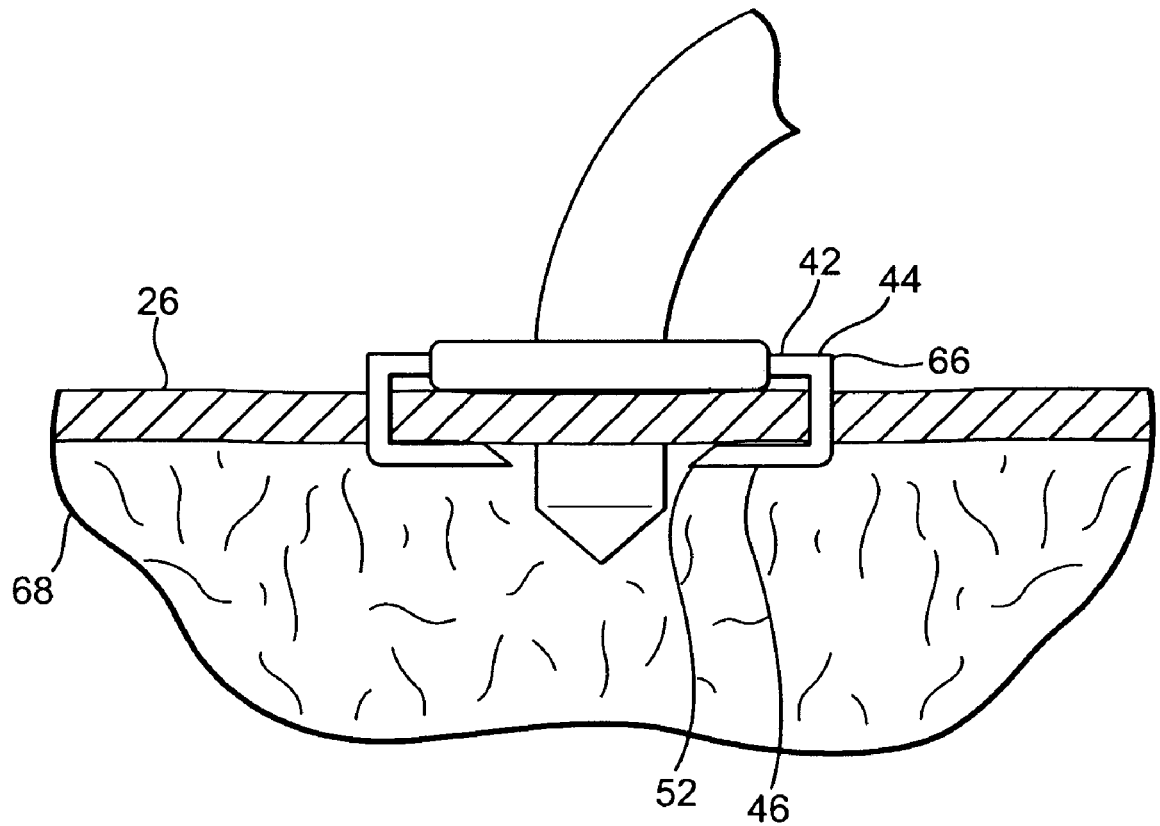
FIG. 5B shows a side plan view of the fastening device of FIG. 4A after the fastening device has been attached to the epicardial tissue.

FIG. 5B shows a side plan view of the fastening device of FIG. 4A in a deformed or deployed configuration. When a force is applied to the attachment device 58 so that bending sections 62 slide past the support section 60 toward the epicardium 26, the upper sections 44 of tines 42 are bent, creating a bend 66. As shown in FIG. 5B, this bending forces the points 52 of lower sections 46 through the epicardium 26 and into the myocardium 68, thereby securing the fastening device 28 and the electrode 24 to the heart 16. After attachment, the support section 60 of the attachment device 58 can then be slid in direction Y as shown in FIG. 5A, and the fastening device 28 is thereby released from the attachment device 58.

Figure 6A:
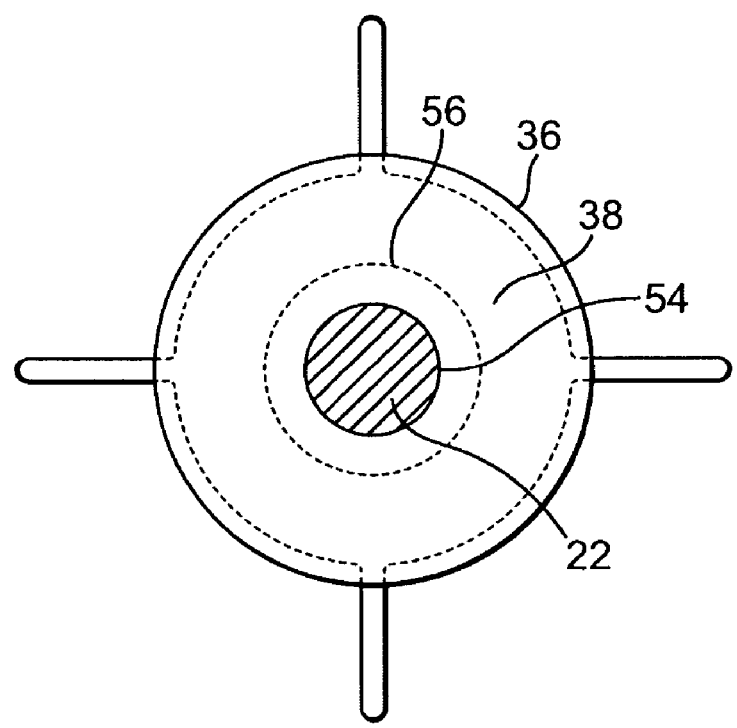
FIG. 6A shows a top plan view of another embodiment of the present invention.
Figure 6B:
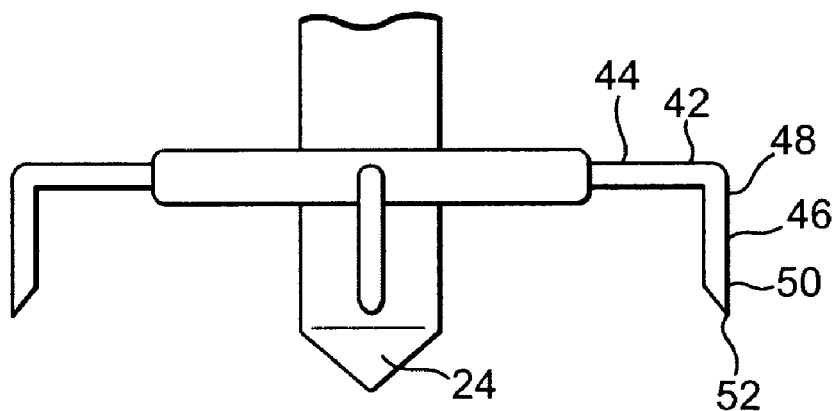
FIG. 6B shows a side plan view of the fastening device of FIG. 6A.

FIGS. 6A-6B show yet another alternative embodiment of the present invention. In this embodiment, the platform 38 has a substantially annular shape and includes an aperture 56. The housing 36 encompassing the platform 38 is also substantially annular and includes an aperture 54. The lead body 22 passes through the apertures 54 and 56. Tines 42 extend from the platform 38. The tines 42 have an upper section 44 and a lower section 46. The lower sections 46 have proximal ends 48 and distal ends 50. The points 52 for piercing the epicardium 26 can be located at the distal ends 50.

Although four tines 42 are shown in FIGS. 6A and 6B, the number of tines 42 may vary. In one embodiment, the tines 42 are spaced at approximately 90 degrees from each other. The angle between the upper sections 44 and the lower sections 46, as well as the angle between the upper sections 44 and the platforms 38 may also vary. In one embodiment, the angle between the upper sections 44 and the lower sections 46 can range from approximately 70 to approximately 120 degrees. In one embodiment, the penetration of the electrode 24 into the epicardium 26 can range from approximately 0 to 10 millimeters. In one embodiment, the ratio of the diameter of the platform 38 to the diameter of the lead body 22 can vary between about 2:1 and about 4:1.

Figure 7A:
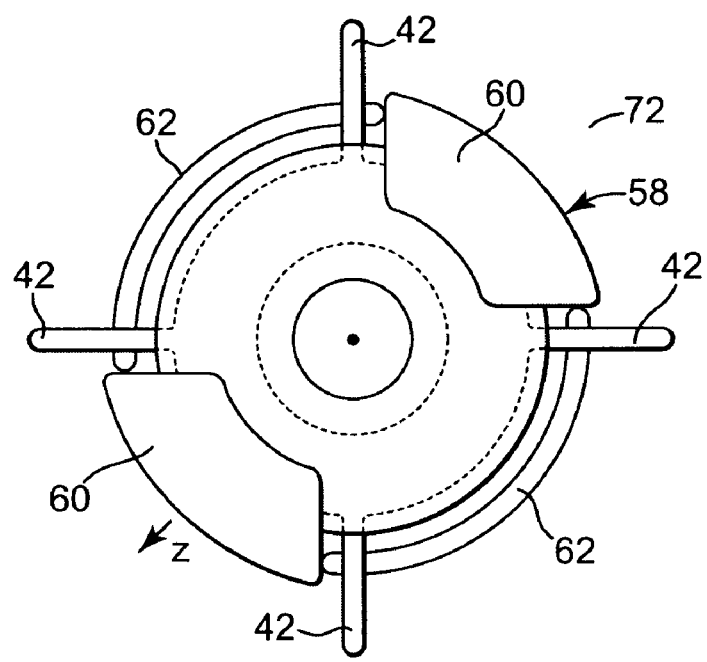
FIG. 7A shows a bottom plan view of the fastening device of FIG. 6A positioned for attachment in the attachment device prior to attachment.

FIG. 7A shows the fastening device of FIGS. 6A and 6B after it has been positioned in the attachment device 58. The attachment device includes support sections 60 and bending sections 62. The fastening device 28 is interposed between the support sections 60 and the bending sections 62. The bending sections 62 overlay the tines 42. During deployment, the support sections 60 are located adjacent to the epicardium 26 and retain the fastening device 28 by clamping onto the fastening device 28.

Figure 7B:
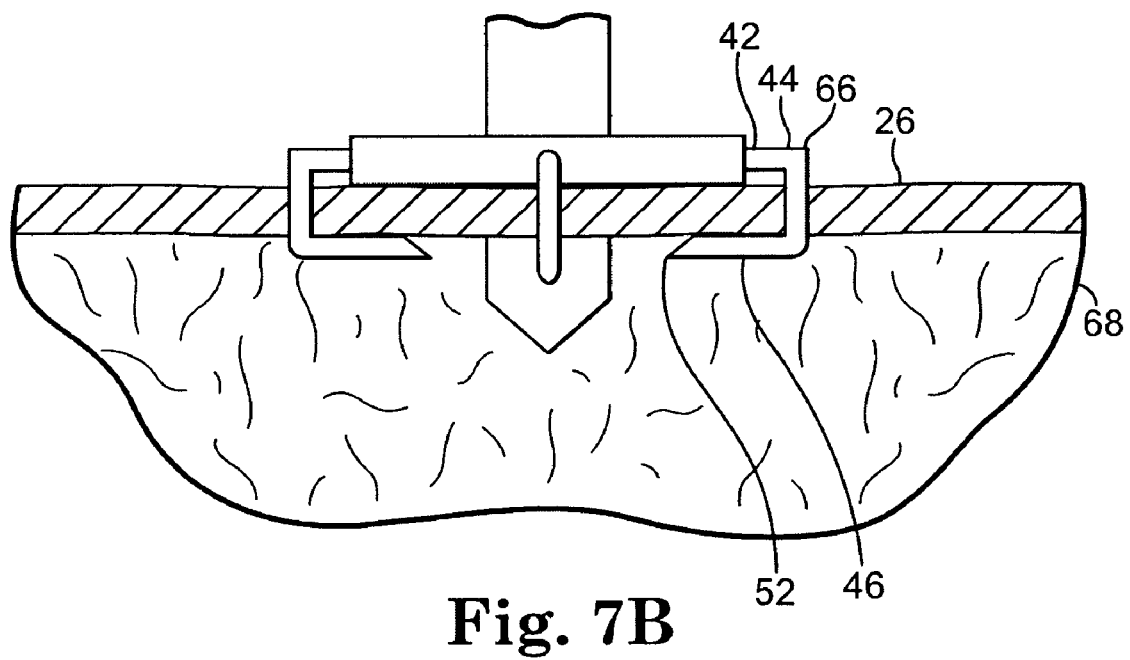
FIG. 7B shows a side plan view of the fastening device of FIG. 6A after the fastening device has been attached to the epicardial tissue.

FIG. 7B shows a side plan view of the fastening device of FIG. 6A in a deformed or deployed configuration. When a force is applied to the attachment device 58 so that the bending sections 62 slide past the support sections 60 toward the epicardium 26, a bend 66 is created in the upper sections 44 of tines 42. As shown in FIG. 7B, this bending forces the points 52 of lower sections 46 through epicardium 26 and into the myocardium 68, thereby securing the fastening device 28 and the electrode 24 to the heart 16. After attachment, the support sections 60 of the attachment device 58 move in direction z shown in FIG. 7A, thus releasing the fastening device 28.

Figure 8:
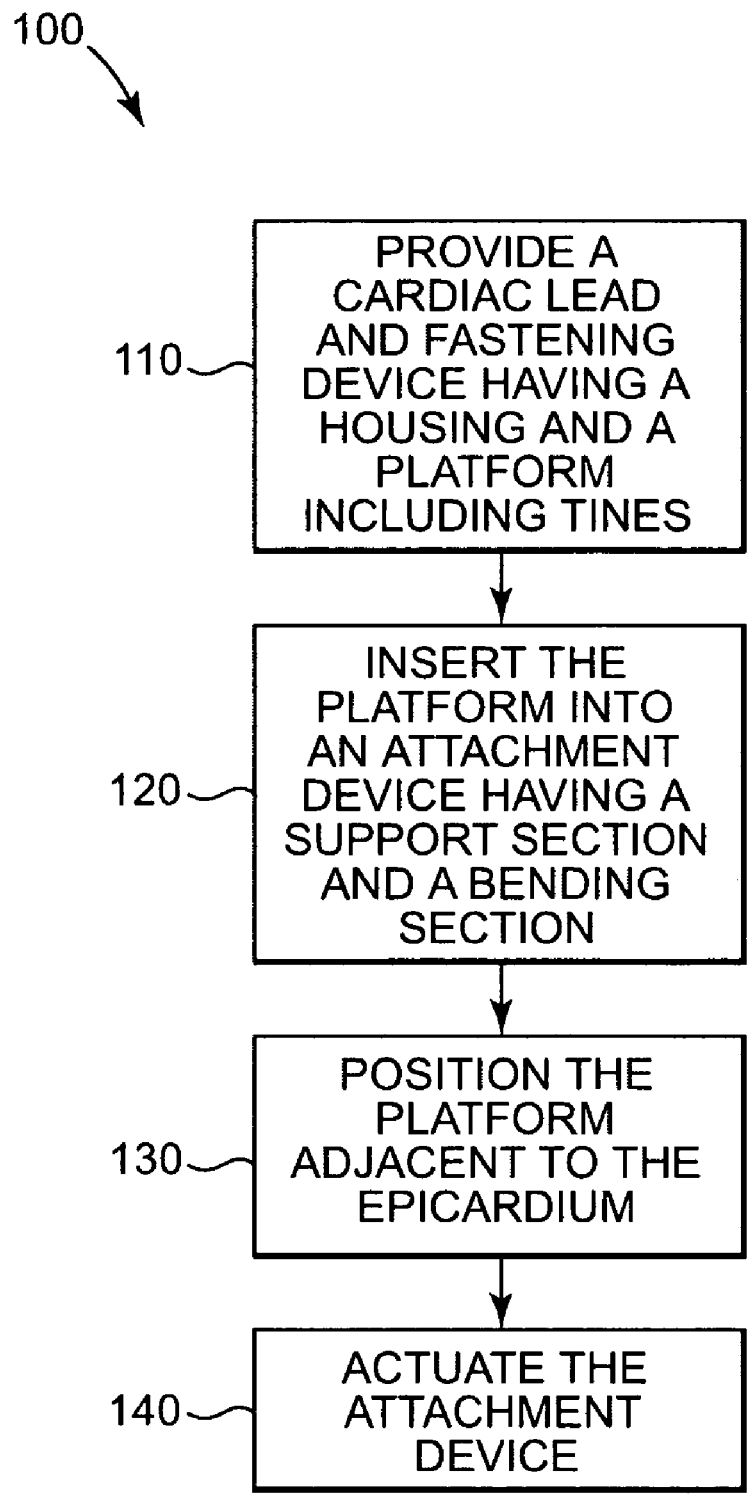
FIG. 8 shows a flowchart describing a method of using an epicardial lead.

FIG. 8 depicts an exemplary implantation process 100 for attaching the cardiac lead 14 to the heart 16. The cardiac lead may be implanted using any technique known in the art. Exemplary techniques include a thoracotomy/thorascopic approach and an endoscopic subxiphoid surgical procedure, such as is disclosed in U.S. Patent Publication 2004/0111101 A1 to Chin, which is hereby incorporated by reference. As shown, a cardiac lead 14 and a fastening device 28 having a platform 38 and housing 36 are provided (block 110). The platform 38 is inserted into an attachment device 58 having a support section 60 and bending sections 62 (block 120). The fastening device 28 may be slideably inserted into the attachment device 58 (see FIGS. 3A and 5A) or it may be clamped by the attachment device 58 (see FIG. 7A). The platform 38 is then located adjacent to the epicardium 26 so that the tines 42 are positioned to pierce the epicardium 26 (block 130). The attachment device 58 is actuated, causing the bending section 62 to slide past the support section 60, thus bending lower sections 46 of tines 42 and thereby attaching the fastening device 28 to the heart 16 (block 140).

Figure 9A:
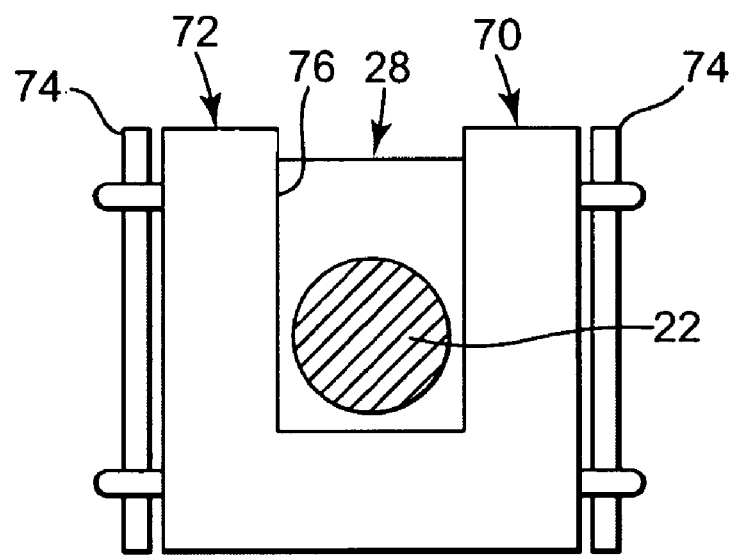
FIG. 9A shows a top plan view of the fastening device of FIG. 2A positioned for removal in a removal device.

FIG. 9A shows a top plan view of the fastening device 28 of FIG. 2A positioned for removal in a removal device 70. As shown in FIG. 9A, the removal device 70 includes a support section 72 and bending sections 74. The fastening device 28 is interposed between the support section 72 and the bending sections 74. During removal, the bending sections 74 are positioned adjacent to the epicardium 26. The support section 72 includes an opening 76 adapted to fit around the lead body 22. When the removal device 70 is actuated, the bending sections 74 slide past the support section 72 and away from the epicardium 26.

Figure 9B:
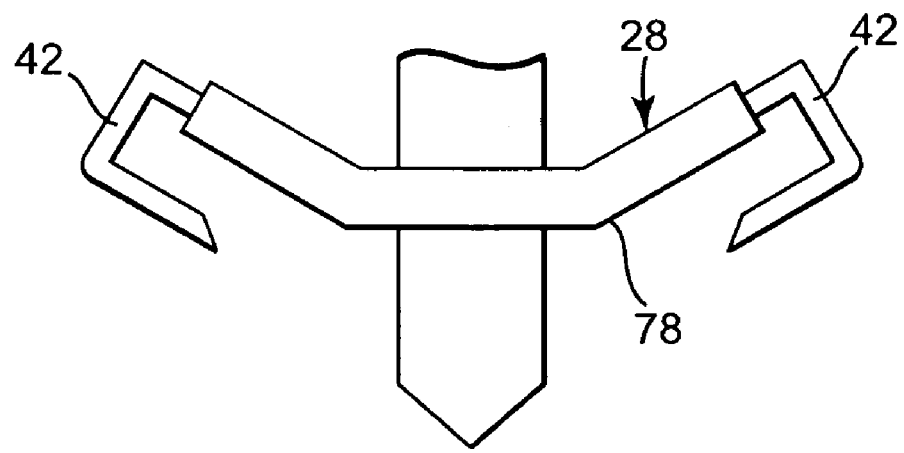
FIG. 9B shows a side plan view of the fastening device of FIG. 2A after removal.

FIG. 9B shows a side plan view of the fastening device of FIG. 2A after removal. As bending sections 74 slide past the support section 72, a bend 78 is created in the fastening device 28 and the tines 42 are pulled out of the heart 16. As shown, the removal device 70 is adapted to pull four tines 42 out of the epicardium 26, but the removal device 70 can pull as many tines 42 as is necessary.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

I claim:

1. An epicardial pacing lead comprising:
   a flexible, elongated lead body having a proximal end and a distal end;
   an electrode coupled to the lead body near the distal end;
   a housing coupled to the lead body proximal to the electrode; and
   a malleable metal platform at least partially encompassed by, and permanently secured within, the housing, the platform including at least four bendable tines, each tine configured for penetrating the epicardium and including an upper section extending outwardly from the platform in a plane generally parallel to the platform and a lower section extending distally at an angle to the upper section, wherein the upper section of the tines is connected directly to the platform.

2. The epicardial pacing lead of claim 1 wherein the housing is integral with the lead body.

3. The epicardial pacing lead of claim 1 wherein the platform has a substantially annular shape and the housing has a substantially annular shape and wherein the tines are spaced approximately 90 degrees apart around the lead body.

4. The epicardial pacing lead of claim 1 wherein the housing has a substantially rectangular shape and the platform has a substantially rectangular shape.

5. The epicardial pacing lead of claim 1 wherein the angle between the tine lower section and the tine upper section is approximately between about 70 and about 120 degrees.

6. The epicardial pacing lead of claim 3 wherein the ratio of the outer radius of the platform to the diameter of the lead is between about 2:1 and about 4:1.

7. The epicardial pacing lead of claim 1 wherein the electrode includes a distal end and wherein the distance between the platform and the electrode distal end is between approximately 0 and 10 mm.

8. An epicardial pacing lead comprising:
   a flexible, elongated lead body having a proximal end and a distal end;
   an electrode coupled to the lead body near the distal end;
   a housing coupled to the lead body proximal to the electrode;
   a malleable metal platform defining a first plane, the platform at least partially encompassed by, and permanently secured within, the housing; and
   bendable means for penetrating the epicardium extending from the platform, at least a portion of the bendable means generally disposed in the first plane.

9. The epicardial pacing lead of claim 8 wherein the bendable means for penetrating includes at least four bendable tines, each tine having an upper section and a lower section.

10. The epicardial pacing lead of claim 9 wherein the angle between the tine lower section and the tine upper section is approximately between about 70 and about 120 degrees.

11. The epicardial pacing lead of claim 8 wherein the electrode includes a distal end and wherein the distance between the means for penetrating and the electrode distal end is between approximately 0 and 10 mm.

12. An epicardial pacing lead comprising:
a flexible, elongated lead body having a proximal end and a distal end;
an electrode coupled to the lead body near the distal end;
a housing coupled to the lead body proximal to the electrode; and
a malleable metal platform, the platform defining a first plane, the platform permanently secured within the housing, a portion of the platform located within the housing, the platform including a plurality of bendable tines, each tine configured for penetrating the epicardium and including a first section extending from the platform generally in the first plane and a second section extending distally at an angle to the first section.

13. The epicardial pacing lead of claim 12 wherein the housing is integral with the lead body.

14. The epicardial pacing lead of claim 12 wherein the platform and the housing both have a substantially annular shape and the platform has four tines spaced approximately 90 degrees apart around the lead body.

15. The epicardial pacing lead of claim 12 wherein the housing has a substantially rectangular shape and the platform has a substantially rectangular shape.

16. The epicardial pacing lead of claim 12 wherein the first sections are bent so that they extend outwardly from the platform at an angle below the platform.

17. The epicardial pacing lead of claim 12 wherein the first sections are bent so that they extend outwardly from the platform at an angle above the platform.

18. The epicardial pacing lead of claim 12 wherein the plurality of tines is at least five tines.

19. The epicardial pacing lead of claim 12, wherein the platform has a first region defining the first plane and a second region defining a second plane and wherein a first plurality of tines extends from the platform in the first plane and a second plurality of tines extends from the platform in the second plane.

* * * * *